United States Patent [19]

Dillon

[11] Patent Number: 5,759,560
[45] Date of Patent: Jun. 2, 1998

[54] SILICONE THERMOPLASTIC SHEETING FOR SCAR TREATMENT AND USEFUL ARTICLE THEREOF; PROCESS OF MANUFACTURE AND USE

[75] Inventor: Mark E. Dillon, Huntngdon Valley, Pa.

[73] Assignee: Bio Med Sciences, Inc., Bethlehem, Pa.

[21] Appl. No.: 508,116

[22] Filed: Jul. 27, 1995

[51] Int. Cl.$^6$ .............. A01N 25/34; A61F 13/02; A61L 15/16
[52] U.S. Cl. .............. 424/402; 424/448; 424/449; 427/387
[58] Field of Search .............. 424/402, 448, 424/449; 427/387

[56] References Cited

U.S. PATENT DOCUMENTS

| | | | |
|---|---|---|---|
| 4,832,009 | 5/1989 | Dillion | 128/156 |
| 4,983,395 | 1/1991 | Chang et al. | 424/448 |

*Primary Examiner*—Thurman K. Page
*Assistant Examiner*—Kathryne E. Shelborne
*Attorney, Agent, or Firm*—John F. A. Earley; John F. A. Earley, III; Harding, Earley, Follmer & Frailey

[57] ABSTRACT

A thermoplastic splinting material with a uniform skin contacting layer of silicone elastomer which accurately contours complex anatomical geometries and is suitable for use in the treatment of dermatologic scars. The product is manufactured in sheet form and may be custom shaped to fit the unique contours of an individual patient by a technician at the clinical site.

10 Claims, 1 Drawing Sheet

SILICONE THERMOPLASTIC SHEETING FOR SCAR TREATMENT AND USEFUL ARTICLE THEREOF; PROCESS OF MANUFACTURE AND USE

BACKGROUND OF THE INVENTION

1. Field of the Invention

This invention relates to a composite material consisting of two layers; a soft silicone elastomer bonded to a thermoplastic sheet. The thermoplastic sheet may be shaped to fit anatomical contours, with the silicone elastomer being placed in contact with the patient's skin. The product is useful for the management of hypertrophic scars or keloids.

2. Description of the Prior Art

Thermoplastic splints have a long history of use in the medical field as shaped articles for the purpose of immobilizing an anatomical region of the body. These materials are also used in the medical field to manage dermal scarring from traumatic injuries such as burns, particularly of the face. The splinting material serves to apply pressure over the region to minimize hypertrophic or keloid scar formation. In facial burn cases, the splinting material is usually formed over a plaster mold of the patient's face. Straps or other devices are typically used to fix the shaped article in place. The contours of the mold may be sculpted and the thermoplastic may be reshaped from time to time as to guide the patient's soft tissue into forming desired contours.

For non-articulating areas of the body, a rigid article is used to transfer stress from the point of application to the entire surface of the device. Alternatively, a semi-rigid product may be used so that a moderate amount of pressure may be applied to an anatomic region without completely restricting movement. Thermoplastic foam materials are sometimes used for this purpose, particularly for the axilla, hands, or neck areas.

As disclosed in my co-pending application Ser. No. 08/200,152, filed Feb. 23, 1994, silicone elastomer materials are also used in the medical field for the management of dermal scarring. These silicone materials soften scar tissue and improve the cosmetic as well as functional aspects of such scars. The biological mechanism for this effect is poorly understood. It is, however, known that the therapeutic benefit is derived independently of pressure applied to the scar surface. For this reason, silicone sheeting materials are most advantageously used on anatomical areas where the application of pressure is restricted or ineffective, such as the neck or abdomen.

It is common practice in the medical field to combine pressure therapy with silicone sheeting in highly critical areas such as the hands or face. In this fashion, a maximum effect can be achieved in a minimum amount of time.

Difficulties arise in combining the two therapies for several reasons. Silicone sheeting materials of the prior art tend to be either thick or stiff for durability purposes. With either case, it is difficult to closely contour such sheeting materials to complex anatomic regions such as the face. Folds or gaps tend to be formed in the silicone sheeting. These inconstancies can cause excessive or inadequate pressure to localized areas of soft tissue when used with a pressure application device, particularly over bony prominences.

My co-pending application discloses an interpenetrating polymer network (IPN) of silicone and polytetrafluoroethylene (PTFE) which has improved physical properties while having decreased thickness. While it is possible to apply the IPN material over facial contours without folds or gaps, it is extremely tedious to do so. The sheets must be cut into complex shapes and meticulously applied to the patients skin to achieve uniform pressure and contact under a pressure application device.

For the purposes of this invention, the terms silicone elastomer, silicone gel, silicone copolymer, or silicone IPN will be equivalent and used interchangeably, since it is believed that this invention may be accomplished with any of these materials. Furthermore, it is contemplated that other therapeutic agents which work by means of skin contact may be used.

SUMMARY OF THE INVENTION

This invention relates to a composite structure which incorporates the pressure therapy and shaping features of thermoplastic splinting materials with the use of silicone elastomers for scar management.

By applying a surface layer of silicone elastomeric material to one side of a thermoplastic splinting material prior to shape forming, I have unexpectedly discovered that shaped articles can be produced which provide a surface layer of silicone for uniform skin contact even when shaped into complex geometric forms.

The manufacturing process lends itself to large-scale production in that flat sheets are produced for final shape-forming by a qualified technician at the clinical site. This provides for rapid and cost effective production of custom made shapes for any given patient.

This invention is an improvement over prior art in that (a) the silicone layer is bonded to the surface of the thermoplastic splinting material, (b) the product is easily shaped without creating folds or gaps between the silicone sheeting and soft tissue, (c) the amount of pressure applied to localized areas under a pressure application device is made uniformly by the presence of the silicone elastomer, (d) both pressure and silicone therapies are applied concomitantly without requiring a separate and/or repeated process of fitting both materials individually, and (e) patient compliance may be improved because daily application of the therapy is greatly facilitated.

DETAILED DESCRIPTION OF SEVERAL EMBODIMENTS

Figure 1:
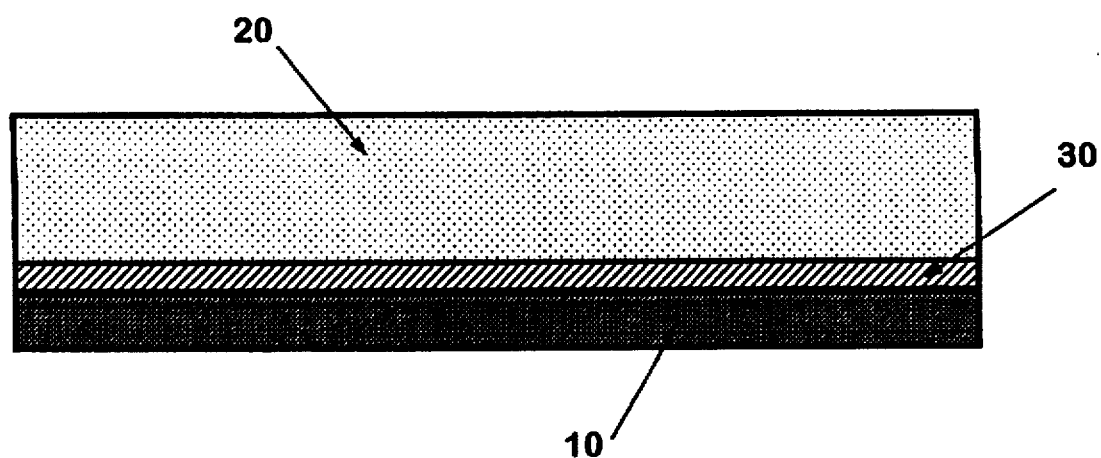
FIG. 1 is a schematic diagram of one embodiment of this invention. A silicone elastomer sheet 10 is bonded to a thermoplastic sheet 20 by means of an adhesive layer 30.

The several embodiments of this invention are described in the following illustrative examples and are not intended to be limiting. Other formulation and constructions will be apparent to those skilled in the art. For example, there are many other silicone compositions that would be suitable for the subject of this invention, either in combination or in blends. Likewise, there are numerous thermoplastic splinting materials which are used in the medical field, many of which may be useful for the purpose of this invention. Furthermore, various thicknesses of thermoplastic materials and silicone layers may be useful. The range of suitable silicone elastomer thickness is between 12.5 microns and 0.5 cm, and that for the adhesive is between 0 and 0.5 cm, since a silicone adhesive could double as a silicone skin contacting surface as well. The primary consideration is that the final construction is not so thin as to have a tendency to wrinkle or otherwise be difficult to handle when shaping.

EXAMPLE 1

A continuous roll of silicone IPN material measuring 0.64 mm in thickness is produced on a polypropylene coated release liner according to established methods. The roll of IPN material is passed through a casting apparatus and coated with 0.15 mm of LSR 30-10:1 liquid silicone rubber from Applied Silicone Corporation of Ventura, Calif. The adhesive coated IPN sheeting material is passed through a tunnel style oven at 1.0 meters per minute at a temperature setting of 75° C. to initiate vulcanization of the adhesive. Upon exiting the tunnel oven, the material is collected and cut into sheets of approximately 80 cm in length. Using a nip-roll apparatus, the sheets of silicone IPN coated with partially vulcanized adhesive are laminated to 1.5 mm thick sheets of rigid polyester thermoplastic splinting material from W-Clear®, Smith & Nephew Rolyan of Germantown, Wis. The silicone IPN laminated sheets of thermoplastic material with a release liner are placed in a convection oven for 1.5 hours at 70° C. to fully vulcanize the adhesive. Then the laminated sheets are allowed to cool.

To apply a laminated sheet to a patient, the release liner is then removed from the silicone IPN surface of one of the laminated thermoplastic sheet. The laminated sheet is placed silicone side down in a convection oven for 5 minutes at 160° C. The heated laminated sheet is then removed from the oven, placed silicone side down over a plaster positive mold of the face of a pediatric burn patient and shaped to the mold. Upon cooling, the shaped material is trimmed and holes are cut for the patient's eyes, nostrils, and mouth to form a face mask. Then the shaped face mask is applied to the face of the patient.

The silicone sheet 10 of the composite product remains fixed to the thermoplastic sheet 20 by the adhesive layer 30. Both the silicone sheet 10 and adhesive layer 30 elongate and compress in localized areas sufficiently to avoid folds or tears. The resulting product is a rigid face mask with a uniform skin contacting sheet 10 of silicone accurately contouring the complex geometry of a human face.

EXAMPLE 2

The process of Example 1 is repeated substituting a 3.2 mm thick semi-rigid thermoplastic foam (Alimed of Dedham, Mass.) for the rigid polyester material.

To apply the laminated sheet, the silicone laminated foam sheet is heated in a convection oven for 5 minutes at 150° C. The heated laminated product is shaped over a plaster mold and allowed to cool as with Example 1. It is trimmed, and holes are cut for the patients eyes, nostrils, and mouth. Then, it is applied to the face of a patient.

The silicone layer of the composite product remains fixed to the thermoplastic foam surface. Both the silicone and adhesive materials elongate and compress in localized areas sufficiently. The resulting product is a semi-rigid face mask with a uniform skin contacting layer of silicone elastomer accurately contouring to the complex geometry of a human face.

I claim:

1. A composite material consisting of two layers for the treatment of dermatologic scars by contacting the skin of patients, comprising a first layer of a therapeutic agent to be placed in uniform skin contact with the skin of the patient, and a second backing layer of a thermoplastic polymer bonded to the first layer to form a composite material capable of being formed into fixed geometric shapes to uniformly cover the skin of patients and to retain those fixed shapes without wrinkling, wherein the polymer of the second backing layer is a rigid sheet of thermoplastic material.

2. A composite material consisting of two layers for the treatment of dermatologic scars by contacting the skin of patients, comprising a first layer of a therapeutic agent to be placed in uniform skin contact with the skin of the patient, and a second backing layer of a thermoplastic polymer bonded to the first layer to form a composite material capable of being formed into fixed geometric shapes to uniformly cover the skin of patients and to retain those fixed shapes without wrinkling, wherein the polymer of the second backing layer is a semi-rigid sheet of thermoplastic material.

3. A composite material for the treatment of dermatologic scars, comprising a first layer of a therapeutic agent, and a second backing layer of a thermoplastic polymer bonded to said first layer to form a composite material capable of being formed into fixed geometric shapes, wherein the therapeutic agent is a silicone containing compound, and the polymer of the second backing layer is a rigid sheet of thermoplastic material, and the fixed geometric shape is a face mask.

4. A composite material for the treatment of dermatologic scars to cover the skin of patients, comprising a first layer of a therapeutic agent having a surface for placement in uniform skin contact with the skin of patients, and a second backing layer of a thermoplastic polymer bonded to the first layer to form a composite material capable of being formed into fixed geometric shapes to cover the skin of patients and to retain said shapes, wherein the therapeutic agent is a silicone containing compound, and the polymer of the second backing layer is a semi-rigid sheet of thermoplastic material.

5. A composite material for the treatment of dermatologic scars to cover the skin of patients, comprising a first layer of a therapeutic agent, and a second backing layer of a thermoplastic polymer bonded to the first layer to form a composite material capable of being formed into fixed geometric shapes to cover the skin of patients and to retain said shapes, wherein the therapeutic agent is an interpenetrating polymer network of silicone and polytetrafluoroethylene, and the polymer of the second layer is a rigid sheet of thermoplastic material.

6. A composite material for the treatment of dermatologic scars to cover the skin of patients, comprising a first layer of a therapeutic agent having a surface for placement in uniform skin contact with the skin of patients, and a second backing layer of a thermoplastic polymer bonded to the first layer to form a composite material capable of being formed into fixed geometric shapes to cover the skin of patients and to retain said shapes, wherein the therapeutic agent is an interpenetrating polymer network of silicone and polytetrafluoroethylene, and the polymer of the second backing layer is a semi-rigid sheet of thermoplastic material.

7. A method of treating dermatologic scars comprising the steps of taking a roll of silicone IPN sheeting material, coating the silicone IPN sheeting material with a layer of liquid silicone rubber adhesive to form an adhesive layer on the IPN sheeting material, passing the adhesive coated IPN sheeting material through a tunnel style oven to partly vulcanize the adhesive layer, cutting said adhesive coated sheeting material with the partly vulcanized adhesive layer into sheets, laminating said sheets of silicone IPN coated with the partially vulcanized adhesive layer to sheets of polyester thermoplastic splinting material to form laminated sheets.

placing the laminated sheets in a convection oven for 1.5 hours at 75° C. to fully vulcanize the adhesive layer, allowing the laminated sheets to cool, placing one of said laminated sheets silicone side down in a convection oven for 5 minutes at 160° C., removing said laminated sheet from the oven, placing said laminated sheet silicone side down over a plaster positive mold of the face of a pediatric burn patient, shaping the laminated sheet to the mold to form a face mask, allowing the face mask to cool, trimming the face mask and cutting holes in the face mask for the patient's eyes, nostrils, and mouth, and applying the face mask to the face of the patient.

8. A method of treating dermatologic scars comprising the steps of taking a roll of silicone IPN sheeting material, coating the silicone IPN sheeting material with a layer of liquid silicone rubber adhesive to form an adhesive layer on the IPN sheeting, passing the adhesive coated IPN sheeting material through a tunnel style oven to partly vulcanize the adhesive layer, cutting said adhesive coated sheeting material with the partly vulcanized adhesive layer into sheets, laminating said sheets of silicone IPN coated with the partially vulcanized adhesive layer to sheets of semi-rigid thermoplastic foam splinting material to form laminated sheets, placing the laminated sheets in a convection oven to fully vulcanize the adhesive layer, allowing the laminated sheets to cool, placing one of the laminated sheets silicone side down in a convection oven for 5 minutes at 160° C., removing the laminated sheet from the oven, placing the laminated sheet silicone side down and shaping it over a plaster positive mold with the face of a pediatric burn patient to form a face mask, allowing the face mask to cool, trimming the face mask and cutting holes in the material for the patient's eyes, nostrils, and mouth, and applying the face mask to the face of the patient.

9. A method of treating dermatologic scars on the skin of a patient comprising the steps of taking a sheet of silicone containing material, forming a surface layer of adhesive on the silicone sheeting material, laminating said adhesive layered silicone sheeting material to sheets of thermoplastic splinting material, allowing the adhesive layer to cure, allowing the laminated sheet to cool, placing a laminated sheet in an oven at a temperature sufficient to cause softening of the thermoplastic splinting material, placing the softened laminated sheet over a positive mold of an anatomical area of a patient and shaping the laminated sheet to the mold to form a splinting device, allowing the molded laminated sheet splinting device to cool, trimming the molded laminated sheet, and applying the molded and trimmed laminated sheet to the skin of a patient.

10. A method of treating dermatologic scars comprising the steps of taking a sheet of silicone containing material, forming a layer of adhesive on the sheet of silicone material, laminating said adhesive layered silicone sheet to a sheet of semi-rigid thermoplastic foam material to form a laminated sheet, allowing the adhesive layer to cure, allowing the laminated sheet to cool, placing the laminated sheet in an oven at a temperature sufficient to cause softening of the semi-rigid thermoplastic foam material, placing the softened sheet over a positive mold of an anatomical area of a patient and shaping the laminated sheet to the mold to form a molded semi-rigid splinting device, allowing the molded sheet device to cool, trimming the molded sheet device, and applying the molded and trimmed sheet device to the skin of a patient.

* * * * *